US007874838B2

(12) United States Patent
Wallis

(10) Patent No.: US 7,874,838 B2
(45) Date of Patent: *Jan. 25, 2011

(54) INSTRUMENT AND PROCESS FOR THE MINIMUM DISTANCE VERIFICATION BETWEEN TEETH FOR THE PLACEMENT OF ONE OR TWO BONE INTEGRATED DENTAL IMPLANTS

(75) Inventor: Antonio Jose Gordils Wallis, Caracas (VE)

(73) Assignee: Innovative Implant Technology, LLC, Weston, FL (US)

( * ) Notice: Subject to any disclaimer, the term of this patent is extended or adjusted under 35 U.S.C. 154(b) by 519 days.

This patent is subject to a terminal disclaimer.

(21) Appl. No.: 11/614,189

(22) Filed: Dec. 21, 2006

(65) Prior Publication Data

US 2007/0243498 A1 Oct. 18, 2007

Related U.S. Application Data

(63) Continuation of application No. 11/068,515, filed on Feb. 28, 2005, now Pat. No. 7,163,396.

(51) Int. Cl.
*A61C 19/04* (2006.01)
(52) U.S. Cl. ...................................................... 433/72
(58) Field of Classification Search .................. 606/96, 606/102; 433/72–76, 3; 7/164, 163; 33/513
See application file for complete search history.

(56) References Cited

U.S. PATENT DOCUMENTS

| | | | |
|---|---|---|---|
| 1,321,129 A | 11/1919 | Schlueter | |
| 1,321,130 A | 11/1919 | Schlueter | |
| 1,380,040 A | 5/1921 | Chayes | |
| 2,634,501 A | 4/1953 | Linet | |
| 2,675,615 A | 4/1954 | Rosenberg | |
| 3,945,377 A | 3/1976 | Kronner | |
| 4,275,893 A | 6/1981 | Bilanceri | |
| 4,299,212 A | 11/1981 | Goodfrooy | |
| 4,803,976 A | 2/1989 | Frigg et al. | |
| 4,841,975 A | 6/1989 | Woolson | |
| 5,019,077 A | 5/1991 | DeBastiani et al. | |
| 5,030,219 A | 7/1991 | Matsen, III et al. | |
| 5,112,336 A * | 5/1992 | Krevolin et al. | 606/96 |
| 5,302,122 A | 4/1994 | Milne | |
| 5,700,267 A | 12/1997 | Urbanski | |

(Continued)

*Primary Examiner*—Cris L Rodriguez
*Assistant Examiner*—Sunil K Singh
(74) *Attorney, Agent, or Firm*—Gordon & Jacobson, PC

(57) ABSTRACT

An instrument which verifies whether the distance between two teeth is the minimum adequate distance for the placement of one or two implants and centers edentulous space for placement of an implant or divides equidistantly the space for the placement of two implants, the instrument having a first sheet with a perforation joined by an extension from one side to one side of a second larger sheet having two perforations and an opposite side from which a handle extends is improved by stops extending from opposite ends of at least one of the one side of the first rectangular sheet or the opposite side of the second rectangular sheet for engaging the teeth in a position that verifies whether the distance between two teeth is the minimum adequate distance for the placement of one or two implants and centers edentulous space for placement of an implant or divides equidistantly the space for the placement of two implants.

13 Claims, 5 Drawing Sheets

U.S. PATENT DOCUMENTS

| | | |
|---|---|---|
| 5,741,133 A | 4/1998 | Gordils et al. |
| 5,769,856 A * | 6/1998 | Dong et al. .................... 606/96 |
| 5,888,065 A | 3/1999 | Sussman |
| 6,123,546 A | 9/2000 | Bergstrom et al. |
| 6,143,012 A | 11/2000 | Gausepohl |
| 6,342,057 B1 * | 1/2002 | Brace et al. .................... 606/96 |
| 6,347,940 B1 * | 2/2002 | Gordils Wallis .............. 433/72 |
| 6,881,059 B2 * | 4/2005 | Wennemann ................ 433/76 |
| 7,163,396 B2 * | 1/2007 | Gordils Wallis .............. 433/72 |
| 2006/0155283 A1 * | 7/2006 | Doherty et al. ............... 606/69 |

* cited by examiner

I

IV

II

V

III

VI

II

III  IV

V  VI

INSTRUMENT AND PROCESS FOR THE MINIMUM DISTANCE VERIFICATION BETWEEN TEETH FOR THE PLACEMENT OF ONE OR TWO BONE INTEGRATED DENTAL IMPLANTS

CROSS-REFERENCE TO RELATED APPLICATIONS

This application is a continuation of U.S. Ser. No. 11/068,515, filed Feb. 28, 2005, now U.S. Pat. No. 7,163,396 which is hereby incorporated herein by reference in its entirety.

BACKGROUND OF THE INVENTION

1. Field of the Invention

This invention relates to instrumentation and methods for confirming that the edentulous space between teeth has the minimum distance necessary for the placement of one or more implants.

2. State of the Art

U.S. Pat. No. 6,347,940 to Gordils provides an instrument for identifying marks that define locations at which placed dental implants will have a minimum desired distance therebetween and relative to neighboring teeth.

However, it is also important to provide guidance as to where to place such marks along the alveolar rim in the bucco-lingual dimension.

Furthermore, it is important to provide guidance with respect to centralization of the distance between two teeth for the implant placement.

In many cases the distance between two teeth can be insufficient for one or two implants, which could generate an exaggerated proximity between the implant(s) and the neighboring teeth, obstructing the prosthetic restoration and creating hygiene problems which may compromise the case prognosis.

The implants are small titanium cylinders that behave as an artificial root, and they may provide:

a method to anchor total upper and lower removable prosthetics;

a method to place total or partial fixed prosthetics; and a method to replace a single tooth.

Step-by-step clinical procedures for use of the implant are:

a) Pre-Medication;
b) Anesthesia;
c) Elevation of the total thickness flap;
d) Placement of the surgical splint;
e) Marking of the implant location;
f) Use of Pilot Drill;
g) Use of progressive diameter drills until reaching the diameter of the selected implant;
h) Placement of the implant; and
i) Second surgical phase for the placement of healing devices once the bone integration period as elapsed.

To these ends, the instrument of co-owned U.S. Pat. No. 6,347,940 has a first sheet which has a centered perforation joined by an extension to a second, larger sheet which has two perforations and, from the larger sheet, an extension joining it to a handle for a process verifying space between teeth. However, the first and second sheets have only their shapes to determine their verification positions and, therefore can be axially offset from one sheet to the other or angularly offset out of their verification positions.

SUMMARY OF THE INVENTION

Therefore, an instrument which verifies whether the distance between two teeth is the minimum adequate distance for the placement of one or two implants, verifies that marks made with a surgical splint have between them the minimum adequate distance, and centers the edentulous space for placement of an implant or divides equidistantly the space for the placement of two implants is provided. The instrument has a first rectangular sheet with a central perforation, a second larger rectangular sheet having two perforations, an extension joining facing sides of the two sheets, and a handle extending from an opposite side of the extension of the second sheet. The instrument includes an improvement of stops extending from opposite ends of at least one of the sheets for engaging the teeth in a position that verifies whether the distance between two teeth is the minimum adequate distance for the placement of one or two implants, verifies that marks made with a surgical splint have between them the minimum adequate distance, and centers edentulous space for placement of an implant or divides equidistantly the space for the placement of two implants.

In the preferred embodiments of the instrument, the stops are two extensions or prolongations added to each of the plates. The purpose or utility obtained at least with this preferred improvement is that, upon introducing the plates with one or two perforations between the teeth, the marks made to the bone are through plates stopped by the teeth. As described in the BACKGROUND above, the basic requirements in the placement of implants is that these be located in an adequate vestibular-lingual or vestibular-palatal position in order to achieve a correct distribution of forces for the prosthesis to be conformed without compromising aesthetic and maintenance conditions.

DESCRIPTION OF PREFERRED EMBODIMENTS

Figure 1:
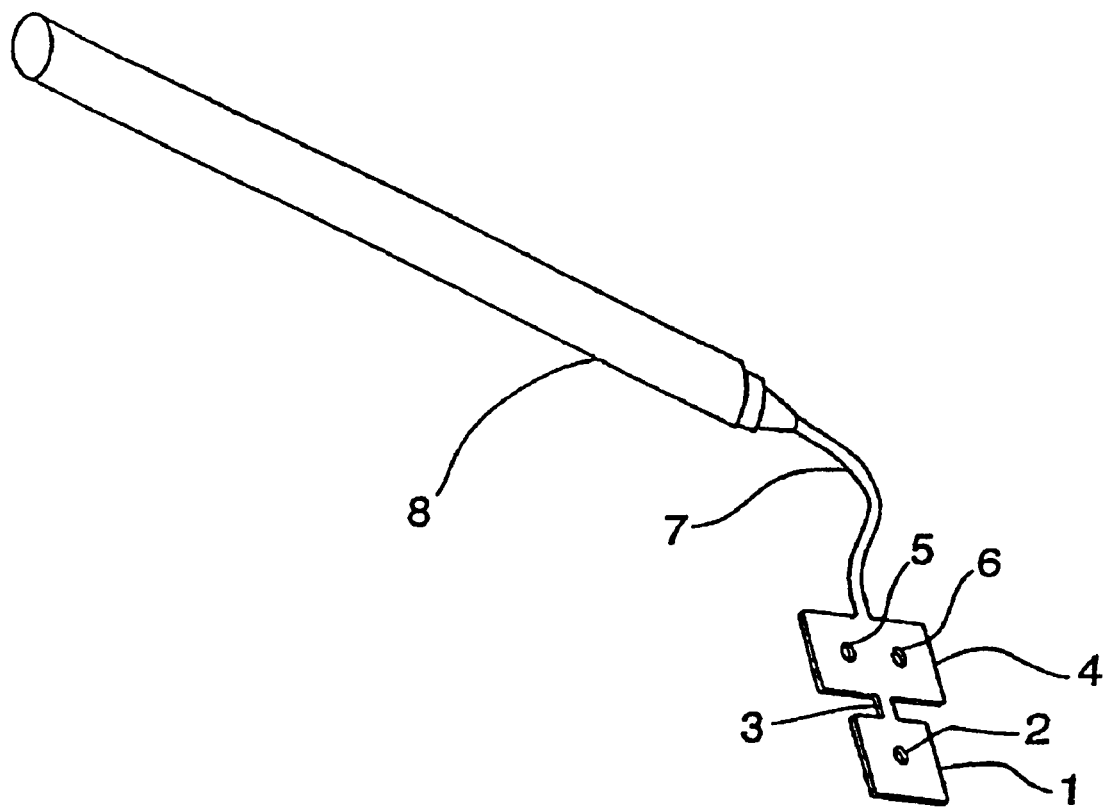
FIG. 1 is a perspective view of a prior art instrument, as described in U.S. Pat. No. 6,347,940.
Figure 2:
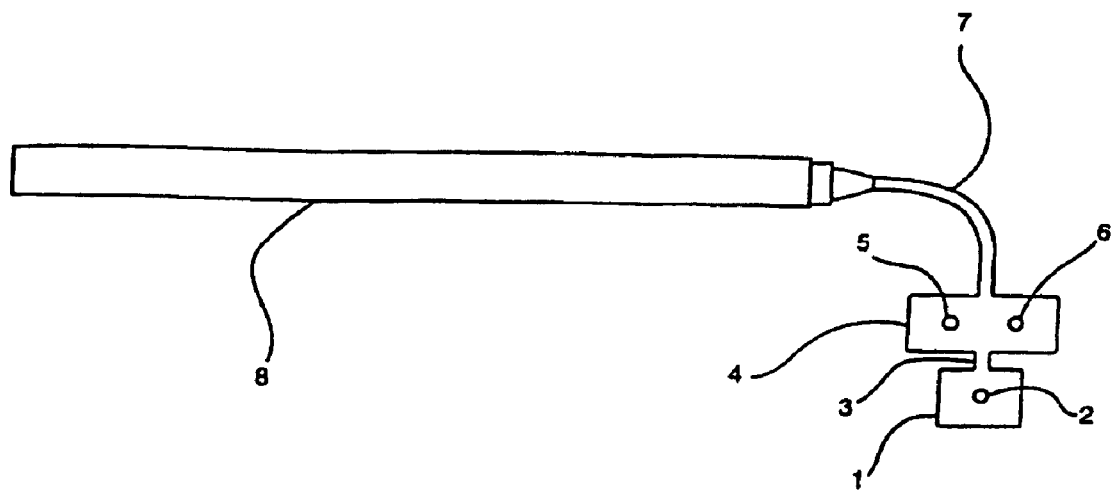
FIG. 2 is an elevational view of the prior art instrument.

FIGS. 1 and 2 show the instrument of co-owned patent U.S. Pat. No. 6,347,940. A first rectangular sheet 1 with a single perforation 2 is connected on one side by a member 3 to one side of a second, larger rectangular sheet 4 having two perforations 5, 6. A member 7 connects an opposite side of the second sheet 4 to one end of a handle 8.

Figure 3:
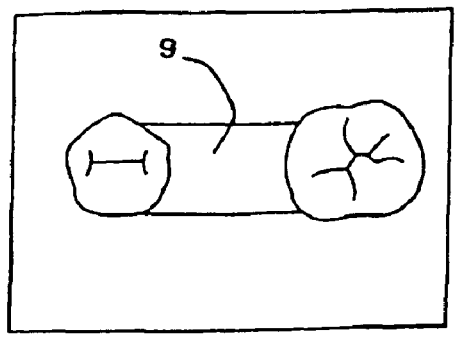
FIG. 3 is a schematic sequence showing the procedure steps in which the prior art instrument is used.
Figure 3:
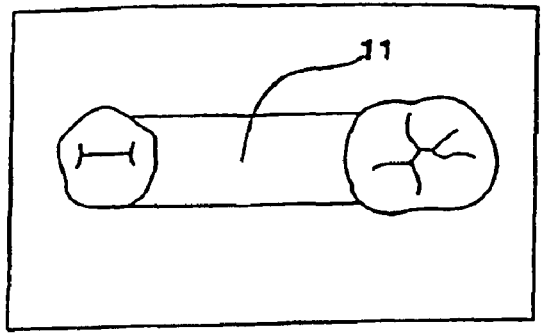
Figure 3:
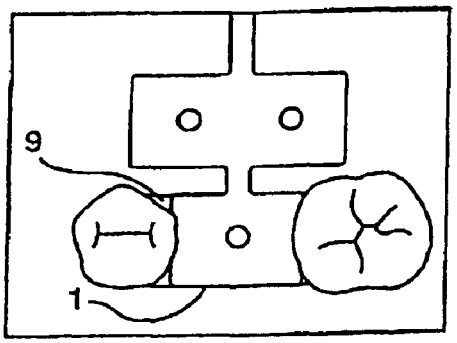
Figure 3:
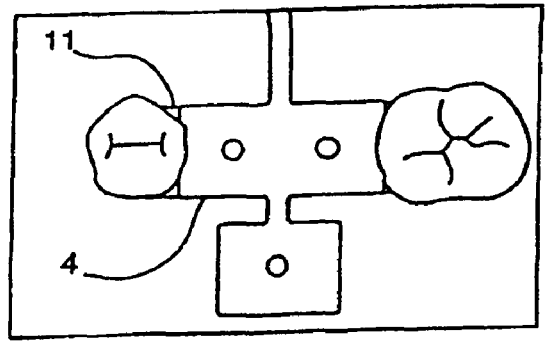
Figure 3:
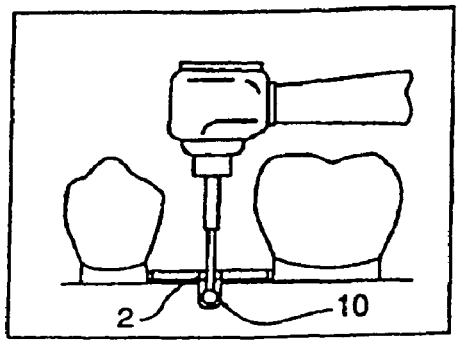
Figure 3:
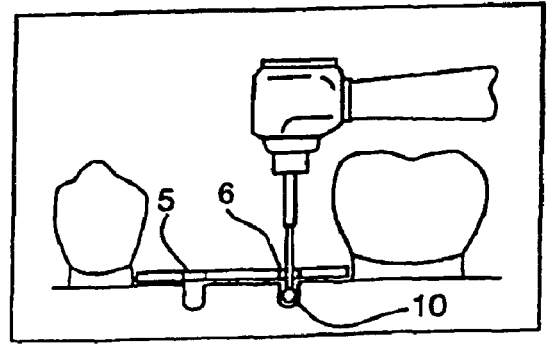

FIG. 3 shows the use of the prior instrument. Specifically, FIG. 3(I) shows the edentulous space 9 between two teeth where the implant will be placed. FIG. 3(II) shows the first sheet 1 with a perforation 2 (FIG. 3(III)) located in the edentulous space 9 between two teeth and the minimum adequate distance is verified for the placement of the implants. FIG. 3(III) shows a round drill 10 through the perforation 2 of the first sheet, thereby marking the bone and achieving an equidistant distribution of the edentulous space. FIG. 3(IV) shows the edentulous space 11 between two teeth where implants will be placed. In FIG. 3(V) the second sheet 4, provided with two perforations, is placed in the edentulous space 11 between the teeth and the minimum adequate distance is verified for the placement of the two implants. FIG. 3(VI) shows a round drill 10 being inserted sequentially through the perforations 5 and 6, thus marking the bone for achieving equidistant distribution of implants in the endentulous space.

Figure 4:
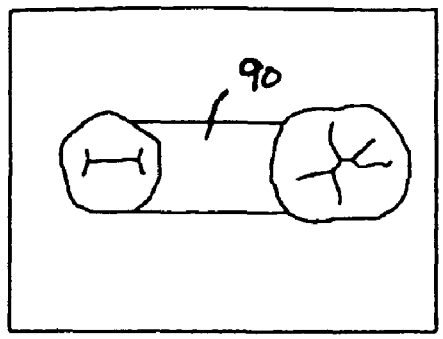
FIG. 4 is a schematic sequence showing the procedure steps in which the instrument of the present invention is used.
Figure 4:
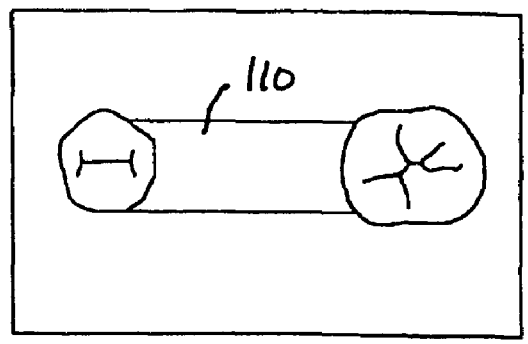
Figure 4:
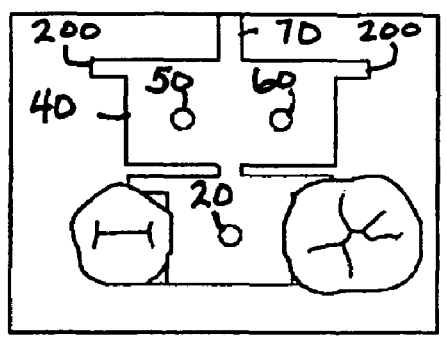
Figure 4:
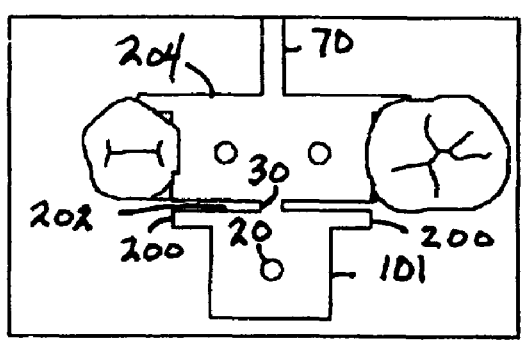
Figure 4:
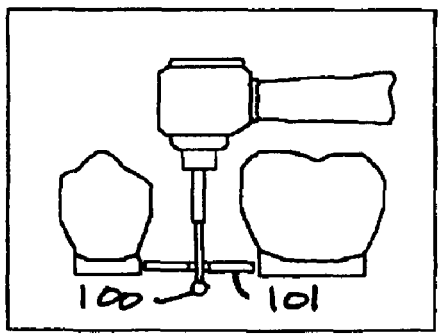
Figure 4:
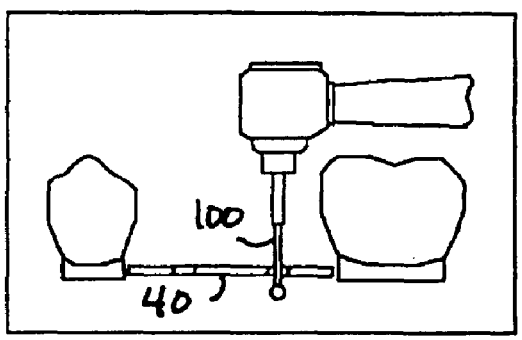
Figure 5:
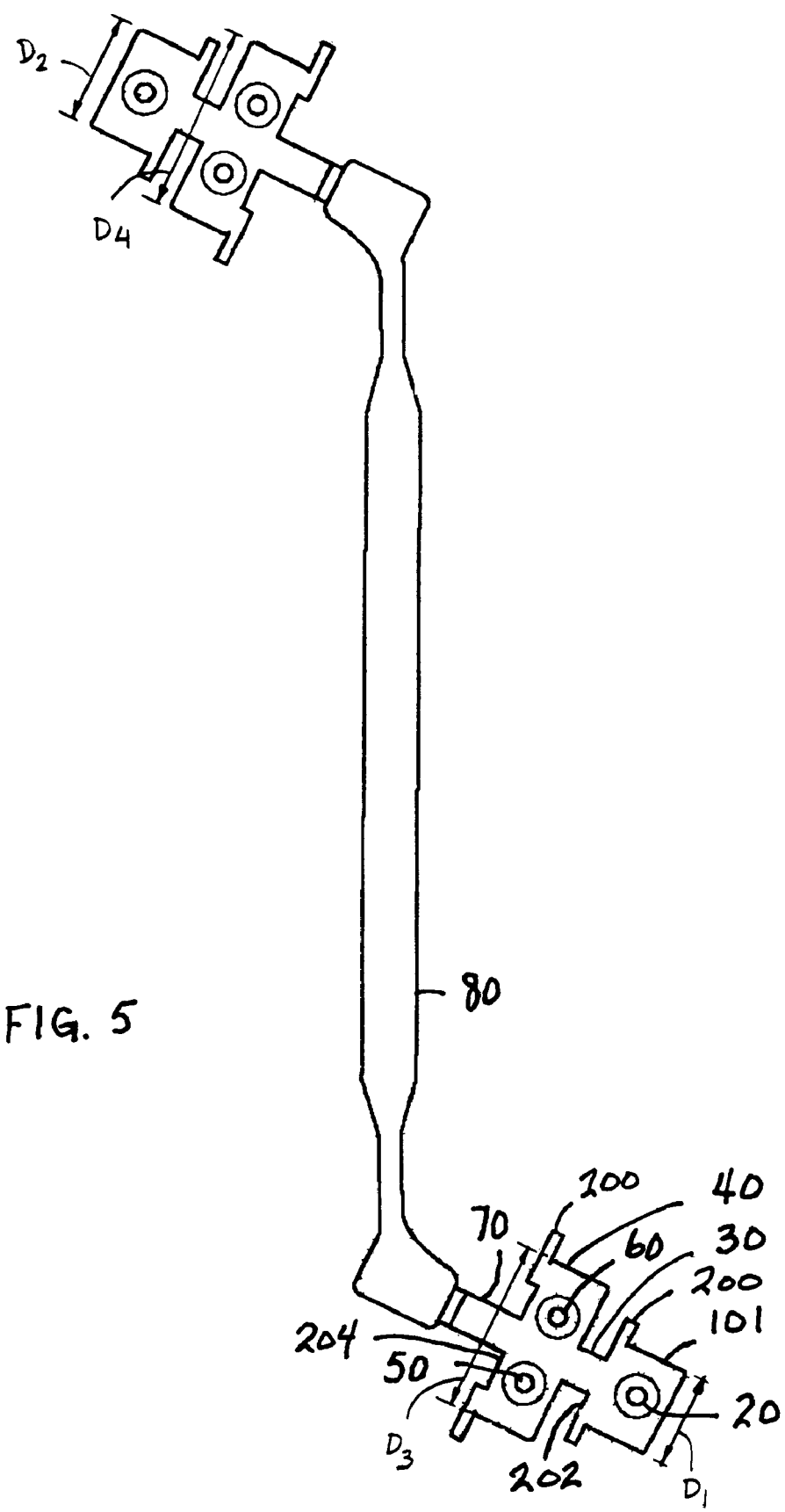
FIG. 5 is a plan view of an instrument according to the invention.

FIGS. 4 and 5 show the instrument of the present invention in at least general correspondence with FIGS. 3 and 1, respectively. Portions of this instrument that correspond to the instrument of U.S. Pat. No. 6,347,940 have corresponding reference characters with the addition of a zero (except first sheets 1 and 101) and, therefore, need not be further described.

FIGS. 4 and 5 show that the present invention improves the instrument with stops 200 extending from opposite ends of at least one side 202 of the first rectangular sheet or the opposite side 204 of the second rectangular sheet for engaging the teeth in a position that verifies the distance between the teeth. The stops 200 engage the teeth on the opposite sides of the edentulous space between the teeth when the first and second sheets are positioned for verifying whether the distance between two teeth is the minimum adequate distance for the placement of one or two implants, verifies that marks made with a surgical splint have amongst them the minimum adequate distance, and centers edentulous space for placement of an implant or divides equidistantly the space for the placement of two implants.

As shown in FIG. 5, sheets corresponding to the first and second sheets 101 and 40 are on the opposite end of the handle 80. The respective first sheets 101 on opposite ends of the handle may have different sizes, particularly a lateral dimension, and the respective second sheets 40 on opposite ends of the handle may have different sizes, particularly a lateral dimension. As such, the lateral dimension $D_2$ of the first sheet at one end of the handle is preferably larger than lateral dimension $D_1$ of the first sheet at the opposite end of the handle, and the lateral dimension $D_4$ of the second sheet at one end of the handle is preferably larger than the lateral dimension $D_3$ of the second sheet at the opposite end of the handle, as shown.

Variations, combinations and permutations of the invention as may occur to those of ordinary skill in the art are contemplated as within the scope of the following claims.

What is claimed is:

1. A dental instrument, comprising:
   a) a handle including first and second ends;
   b) a first sheet provided at said first end of said handle, said first sheet including opposite end walls sized to be positioned between two teeth and including a perforation, said first sheet configured and sized to verify whether the distance between two teeth is a minimum adequate distance for the placement of at least one implant, and center the perforation within a first edentulous space for placement of an implant within the first edentulous space, said first sheet including a first pair of stops extending laterally outward from said opposite end walls which contact the two teeth to prevent passage of the first sheet completely through the first edentulous space; and
   c) a second sheet provided at said first end of said handle, said second sheet including opposite end walls sized to be positioned between two teeth and including two perforations, said second sheet sized and configured such that when placed within a second edentulous space, said second sheet verifies whether the distance between two teeth is a minimum adequate distance for the placement of at least two implants, and said two perforations divides the second edentulous space for placement of two implants within the second edentulous space, said second sheet including a second pair of stops extending from said opposite end walls to prevent passage of the second sheet completely through the second edentulous space,
   wherein said first pair of stops do not extend laterally outward past the opposite end walls of said second sheet.

2. A dental instrument according to claim 1, wherein:
said first and second sheets are coupled by an extension.

3. A dental instrument according to claim 1, further comprising:
   d) a third sheet provided at said second end of said handle, said third sheet including opposite end walls sized to be positioned between two teeth and including a perforation, said third sheet configured and sized to verify whether the distance between two teeth is a minimum adequate distance for the placement of at least one implant, and center the perforation within a third edentulous space for placement of an implant within the third edentulous space, said third sheet including a first pair of stops extending from said opposite end walls which contact the to prevent passage of the third sheet completely through the third edentulous space; and
   e) a fourth sheet provided at said second end of said handle, said fourth sheet including opposite end walls sized to be positioned between two teeth and including two perforations, said fourth sheet sized and configured such that when placed within a fourth edentulous space, said fourth sheet verifies whether the distance between two teeth is a minimum adequate distance for the placement of at least two implants, and said two perforations divides the fourth edentulous space for placement of two implants within the fourth edentulous space, said fourth sheet including a fourth pair of stops extending from opposite end walls to prevent passage of the fourth sheet completely through the fourth edentulous space.

4. A dental instrument according to claim 3, wherein:
said third and fourth sheets are coupled by an extension.

5. A dental instrument, comprising:
   a) a handle including first and second ends; and
   b) a first sheet coupled to said first end of said handle, said first sheet including a lower surface sized for placement on the alveolar rim and opposite lateral sides having front ends defining a front dimension therebetween and rear ends provided with a first pair of stops extending laterally outward from said rear ends, said stops having free ends defining a rear dimension therebetween, said rear dimension greater than said front dimension, said opposite sides spaced to verify whether the distance between two teeth is a minimum adequate distance for the placement of at least one implant, said opposite sides forward of said stops being receivable between the two teeth and into a first edentulous space from a vestibular-lingual or vestibular-palatal direction and said stops arranged to contact a vestibular surface of the two teeth to prevent said first sheet from passage completely through the first edentulous space between the two teeth, and said first sheet provided with at least one perforation which is at a fixed location with respect to said sheet so that when said lower surface is seated on the alveolar rim said at least one perforation centers or divides equidistantly the first edentulous space in a direction transverse to the vestibular-lingual or vestibular-palatal direction for the placement of at least one implant within the first edentulous space.

6. A dental instrument according to claim 5, wherein:
said at least one perforation is exactly one perforation.

7. A dental instrument according to claim 5, wherein:
said sheet is rectangular.

8. A dental instrument according to claim 5, further comprising:
a second sheet including opposite lateral sides having rear ends provided with a second pair of stops extending laterally outward from said opposite rear ends thereof, said first and second sheets coupled together with an extension,
wherein said first sheet includes exactly one perforation such that when said first sheet is placed within the first edentulous space said exactly one perforation on said first sheet centers said edentulous space, and
said second sheet includes exactly two perforations such that when said second sheet is placed within the second edentulous space said exactly two perforation divide said second edentulous space.

9. A dental instrument according to claim 8, wherein:
said first and second sheets are of different sizes.

10. A dental instrument according to claim 5, further comprising:
a second sheet including stops extending from opposite ends thereof, wherein said second sheet is provided at said second end of said handle.

11. A dental instrument according to claim 10, wherein:
said first and second sheet are of different sizes.

12. A dental instrument according to claim 5, wherein:
when said stops contact the vestibular surface of the two teeth, said at least one perforation is centered on the alveolar rim in the vestibular-lingual or vestibular-palatal direction.

13. A dental instrument according to claim 5, wherein:
said sheet has flat upper surface that extends parallel to said lower surface.

* * * * *